United States Patent
Aguilar et al.

(10) Patent No.: US 7,981,148 B2
(45) Date of Patent: Jul. 19, 2011

(54) STENT DELIVERY CATHETER

(75) Inventors: Amiel Aguilar, San Jose, CA (US); Stephen Griffin, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 228 days.

(21) Appl. No.: 12/022,280

(22) Filed: Jan. 30, 2008

(65) Prior Publication Data

US 2008/0294231 A1 Nov. 27, 2008

Related U.S. Application Data

(60) Provisional application No. 60/938,326, filed on May 16, 2007.

(51) Int. Cl.
*A61F 2/06* (2006.01)
(52) U.S. Cl. .................................................. 623/1.11
(58) Field of Classification Search .............. 623/1.11, 623/1.12, 1.23; 606/108
See application file for complete search history.

(56) References Cited

U.S. PATENT DOCUMENTS

| | | | |
|---|---|---|---|
| 4,547,193 A | 10/1985 | Rydell | |
| 4,580,551 A | 4/1986 | Siegmund et al. | |
| 4,998,923 A | 3/1991 | Samson et al. | |
| 5,026,377 A | 6/1991 | Burton et al. | |
| 5,095,915 A | 3/1992 | Engelson | |
| 5,228,441 A | 7/1993 | Lundquist | |
| 5,315,996 A | 5/1994 | Lundquist | |
| 5,322,064 A | 6/1994 | Lundquist | |
| 5,329,923 A | 7/1994 | Lundquist | |
| 5,334,145 A | 8/1994 | Lundquist et al. | |
| 5,360,401 A | 11/1994 | Turnland et al. | |
| 5,383,853 A | 1/1995 | Jung et al. | |
| 5,437,288 A | 8/1995 | Schwartz et al. | |
| 5,445,646 A | 8/1995 | Euteneuer et al. | |
| 5,458,605 A | 10/1995 | Klemm | |
| 5,458,615 A | 10/1995 | Klemm et al. | |
| 5,477,856 A | 12/1995 | Lundquist | |
| 5,507,751 A | 4/1996 | Goode et al. | |
| 5,507,766 A | 4/1996 | Kugo et al. | |
| 5,569,197 A | 10/1996 | Helmus et al. | |

(Continued)

FOREIGN PATENT DOCUMENTS

EP 0 608 853 A2 8/1994

(Continued)

OTHER PUBLICATIONS

Creganna Medical Devices, "Designing Hypotube Shafts," brochure, prior to Feb. 1, 2005, 2 pp.

(Continued)

*Primary Examiner* — Anhtuan T Nguyen
*Assistant Examiner* — Katherine M Shi
(74) *Attorney, Agent, or Firm* — Vidas, Arrett & Steinkraus, P.A.

(57) ABSTRACT

Stent delivery catheters comprising a hypotube, which may be a micromachined member, disposed on an outer portion of an inner member that may be an extruded multi-lumen member. The hypotube may be secured to the inner member. The devices may be adapted for delivering a self expanding stent by providing a restraining structure or device over the stent during delivery. One or more actuating members are provided through a lumen in the inner member to actuate the restraining structure and release the stent. Methods of use of such catheters are also described.

10 Claims, 15 Drawing Sheets

U.S. PATENT DOCUMENTS

| | | | |
|---|---|---|---|
| 5,573,520 A | 11/1996 | Schwartz et al. | |
| 5,741,429 A | 4/1998 | Donadio, III et al. | |
| 5,772,669 A | 6/1998 | Vrba | |
| 5,788,707 A | 8/1998 | Del Toro et al. | |
| 5,833,632 A | 11/1998 | Jacobsen et al. | |
| 5,968,069 A | 10/1999 | Dusbabek et al. | |
| 6,004,279 A | 12/1999 | Crowley et al. | |
| 6,014,919 A | 1/2000 | Jacobsen et al. | |
| 6,017,319 A | 1/2000 | Jacobsen et al. | |
| 6,036,670 A | 3/2000 | Wijeratne et al. | |
| 6,042,588 A | 3/2000 | Munsinger et al. | |
| 6,048,339 A | 4/2000 | Zirps et al. | |
| 6,068,635 A | 5/2000 | Gianotti | |
| 6,077,295 A | 6/2000 | Limon et al. | |
| 6,096,045 A | 8/2000 | Del Toro et al. | |
| 6,102,890 A | 8/2000 | Stivland et al. | |
| 6,102,932 A | 8/2000 | Kurz | |
| 6,123,712 A | 9/2000 | Di Caprio et al. | |
| 6,168,617 B1 | 1/2001 | Blaeser et al. | |
| 6,174,327 B1 | 1/2001 | Mertens et al. | |
| 6,203,558 B1 | 3/2001 | Dusbabek et al. | |
| 6,241,758 B1 | 6/2001 | Cox | |
| 6,245,098 B1 | 6/2001 | Feeser et al. | |
| 6,260,458 B1 | 7/2001 | Jacobsen et al. | |
| 6,280,465 B1 | 8/2001 | Cryer | |
| 6,287,291 B1 | 9/2001 | Bigus et al. | |
| 6,287,315 B1 | 9/2001 | Wijeratne et al. | |
| 6,302,893 B1 | 10/2001 | Limons et al. | |
| 6,315,790 B1 | 11/2001 | Gerberding et al. | |
| 6,325,814 B1 | 12/2001 | Euteneuer et al. | |
| 6,342,066 B1 | 1/2002 | Toro et al. | |
| 6,368,344 B1 | 4/2002 | Fitz | |
| 6,371,962 B1 | 4/2002 | Ellis et al. | |
| 6,387,075 B1 | 5/2002 | Stivland et al. | |
| 6,391,050 B1 | 5/2002 | Broome | |
| 6,398,802 B1 | 6/2002 | Yee | |
| 6,425,898 B1 * | 7/2002 | Wilson et al. | 606/108 |
| 6,428,489 B1 | 8/2002 | Jacobsen et al. | |
| 6,428,566 B1 | 8/2002 | Holt | |
| 6,431,039 B1 | 8/2002 | Jacobsen et al. | |
| 6,440,088 B1 | 8/2002 | Jacobsen et al. | |
| 6,475,209 B1 | 11/2002 | Larson et al. | |
| 6,485,515 B2 | 11/2002 | Strecker | |
| 6,514,280 B1 | 2/2003 | Gilson | |
| 6,517,569 B2 | 2/2003 | Mikus et al. | |
| 6,530,947 B1 | 3/2003 | Euteneuer et al. | |
| 6,533,805 B1 | 3/2003 | Jervis | |
| 6,562,064 B1 | 5/2003 | deBeer | |
| 6,576,008 B2 | 6/2003 | Devonec et al. | |
| 6,579,246 B2 | 6/2003 | Jacobsen et al. | |
| 6,592,549 B2 | 7/2003 | Gerdts et al. | |
| 6,592,568 B2 | 7/2003 | Campbell | |
| 6,592,569 B2 | 7/2003 | Bigus et al. | |
| 6,602,280 B2 | 8/2003 | Chobotov | |
| 6,607,555 B2 | 8/2003 | Patterson et al. | |
| 6,610,046 B1 | 8/2003 | Usami et al. | |
| 6,623,491 B2 | 9/2003 | Thompson | |
| 6,629,981 B2 | 10/2003 | Bui et al. | |
| 6,652,508 B2 | 11/2003 | Griffin et al. | |
| 6,660,031 B2 | 12/2003 | Tran et al. | |
| 6,669,716 B1 | 12/2003 | Gilson et al. | |
| 6,676,666 B2 | 1/2004 | Vrba et al. | |
| 6,699,274 B2 | 3/2004 | Stinson | |
| 6,702,802 B1 | 3/2004 | Hancock et al. | |
| 6,712,827 B2 | 3/2004 | Ellis et al. | |
| 6,716,238 B2 | 4/2004 | Elliott | |
| 6,723,071 B2 | 4/2004 | Gerdts et al. | |
| 6,726,714 B2 | 4/2004 | DiCaprio et al. | |
| 6,742,210 B2 | 6/2004 | Hutton et al. | |
| 6,743,219 B1 | 6/2004 | Dwyer et al. | |
| 6,766,720 B1 | 7/2004 | Jacobsen et al. | |
| 6,773,446 B1 | 8/2004 | Dwyer et al. | |
| 6,802,849 B2 | 10/2004 | Blaeser et al. | |
| 6,989,024 B2 * | 1/2006 | Hebert et al. | 623/1.11 |
| 2001/0044633 A1 | 11/2001 | Klint | |
| 2003/0069522 A1 | 4/2003 | Jacobsen et al. | |
| 2003/0093059 A1 | 5/2003 | Griffin et al. | |
| 2003/0125709 A1 | 7/2003 | Eidenschink | |
| 2004/0111044 A1 | 6/2004 | Davis et al. | |
| 2004/0181174 A2 | 9/2004 | Davis et al. | |
| 2005/0288628 A1 | 12/2005 | Jordan et al. | |
| 2006/0030923 A1 | 2/2006 | Gunderson | |
| 2006/0100687 A1 | 5/2006 | Fahey et al. | |
| 2007/0208405 A1 | 9/2007 | Goodin et al. | |
| 2008/0255651 A1 * | 10/2008 | Dwork | 623/1.11 |

FOREIGN PATENT DOCUMENTS

| | | |
|---|---|---|
| EP | 0 937 481 A1 | 8/1999 |
| WO | 95/24236 A1 | 9/1995 |
| WO | 97/44086 A1 | 11/1997 |
| WO | 03/004086 A2 | 1/2003 |

OTHER PUBLICATIONS

"Creganna Self-Expanding Stent Delivery Platform," brochure, prior to Feb. 1, 2005, 1 pp.

Creganna Medical Devices, "Hypotube Device Shafts—Distal Profile Design," brochure, prior to Feb. 1, 2005, 1 pp.

Creganna Medical Devices, "Hypotube Shafts," Feb. 3, 2005, http://www.creganna.com/index.php?module=1hs&id=e369853df766fa44e1ed0ff613f563bd, 3 pp.

Farrissey, Medical Device Technology, publication, "Metal Shafts: Designs to Meet the Required Performance," Dec. 2004, 4 pp.

"Device Shafts," Creganna Medical Devices, Reader Service #69, prior to Feb. 1, 2005, 1 pp.

* cited by examiner

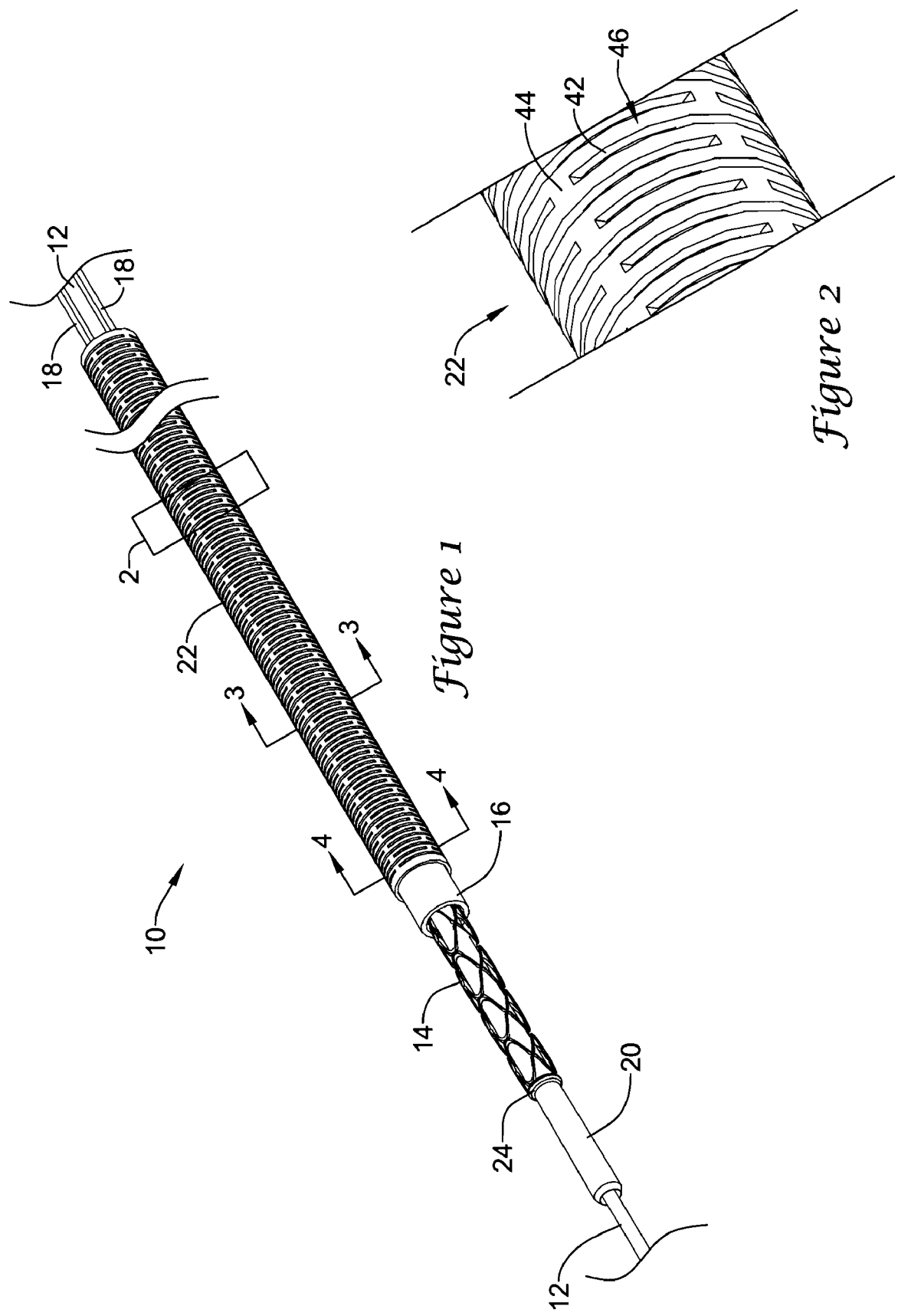

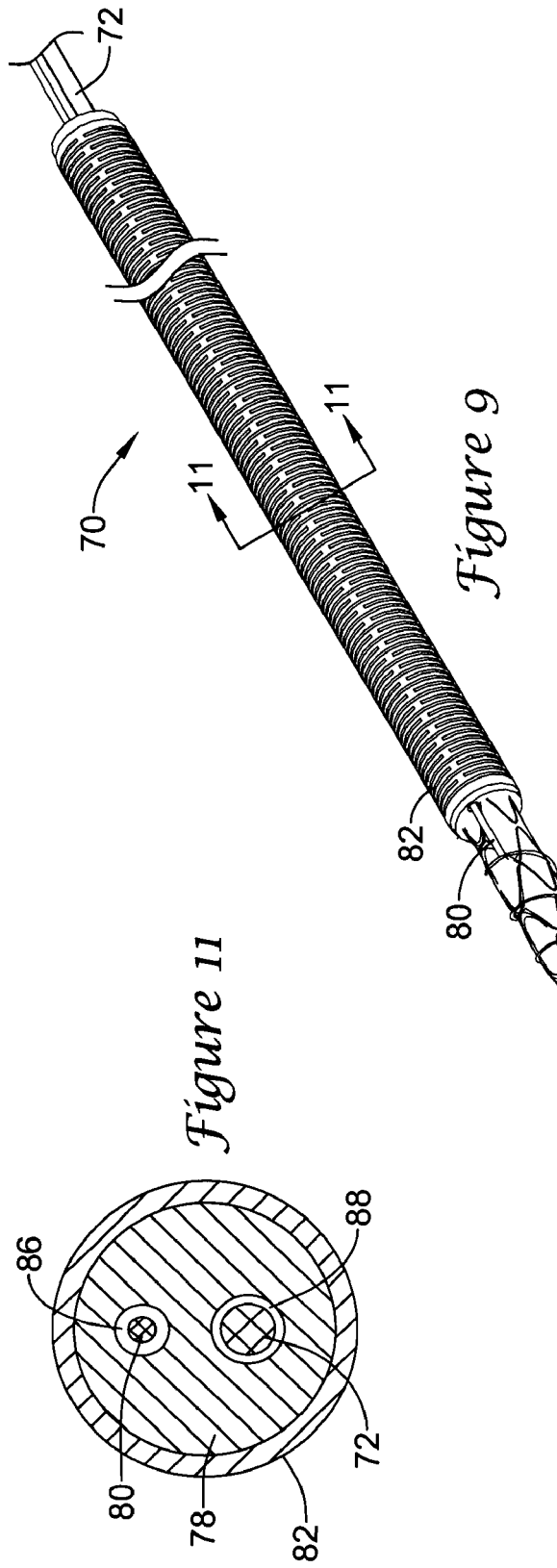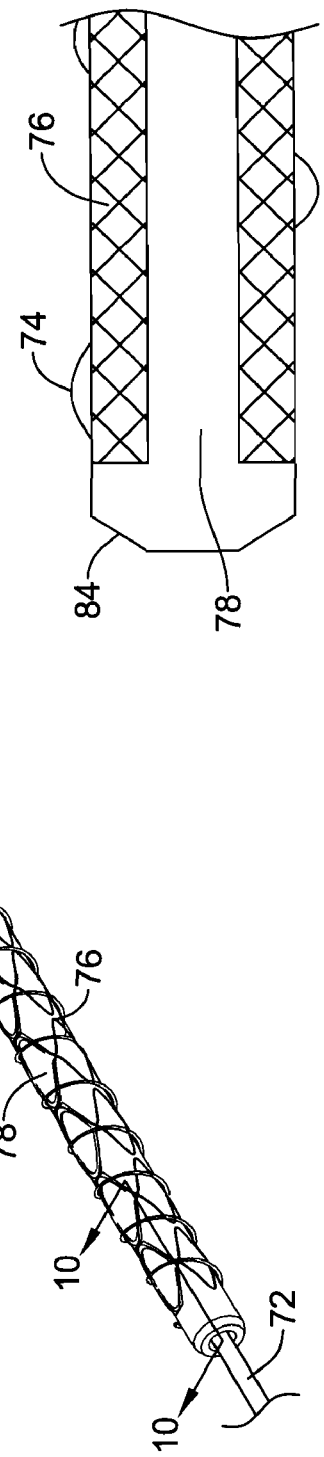

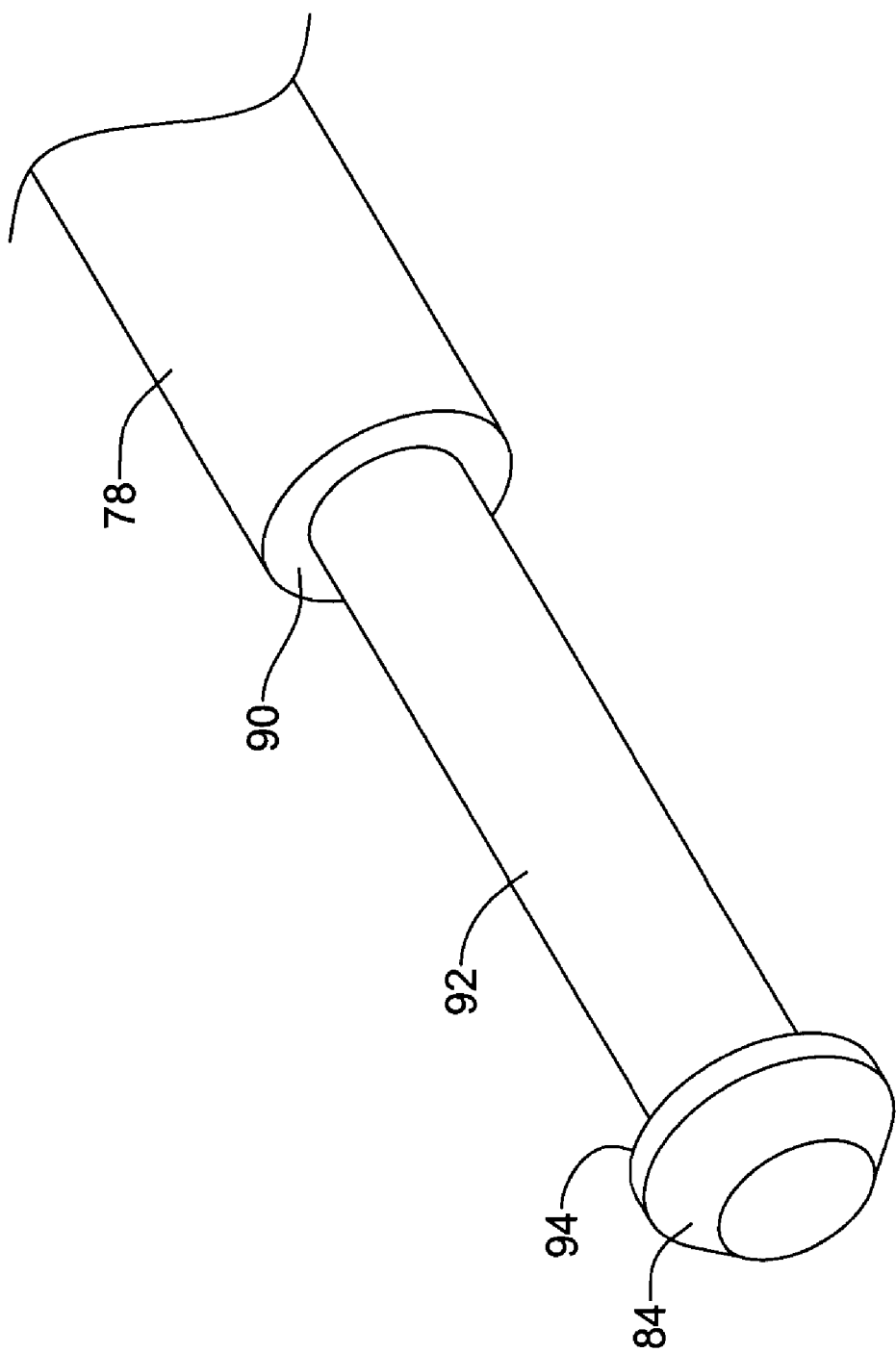

STENT DELIVERY CATHETER

RELATED APPLICATIONS

This application claims the benefit of U.S. Provisional Application Ser. No. 60/938,326, filed May 16, 2007, the entire disclosure of which is incorporated herein by reference.

FIELD

The invention relates generally to catheters and relates more particularly to catheters that are adapted for stent delivery.

BACKGROUND

Medical devices such as catheters may be subject to a number of often conflicting performance requirements such as flexibility and strength. Catheters such as stent delivery catheters are expected to exhibit flexibility so that a patient's vasculature can be navigated sufficiently to access a treatment site. Stent delivery catheters, particularly catheters for delivering self-expanding stents, are also expected to exhibit tensile and/or compressive strength.

A need remains, therefore, for stent delivery catheters adapted to provide both flexibility and strength.

SUMMARY

The present invention, in certain illustrative embodiments, includes a self-expanding stent delivery catheter comprising an elongate inner multi-lumen member and an outer hypotube metallic tube secured thereto. The outer hypotube may include one or more micromachined portions, or may be micromachined over substantially its entire length. The inner member includes at least one lumen adapted to receive a guidewire or other interventional device or media, and at least one ancillary lumen adapted to receive an actuating member that is used in releasing a stent that is releasably secured at a distal position or location of the catheter. The hypotube may extend for a major portion of the catheter length, terminating at a location proximal the distal end. The stent may be secured to the inner, multi-lumen member at a location distal of the distal end of the hypotube.

In one illustrative embodiment, a moveable sheath is disposed on the inner, multi-lumen member such that it may moveably cover the stent, which may be disposed on a portion of the inner member near its distal end. The moveable sheath is secured to at least one actuating member. Prior to implantation and release of the stent, the moveable sheath holds the stent in a compressed state on the inner member. Once the device is advanced to a desired location, the actuating member is used to move the moveable sheath such that it allows the stent to self-expand. Multiple actuating members may be provided in multiple ancillary lumens. During the step of releasing the stent, the hypotube may provide support to accurately release the stent at the desired location.

In another illustrative embodiment, the stent is secured to the inner member by the use of a suture or wire that counters pressure from the stent, holding it in a compressed position. In one such embodiment, a suture is helically wrapped about the stent, with one end of the suture secured to the inner, multi-lumen member, and the other end secured to an actuating member. On actuation of the actuating member, the suture is released, allowing the stent to expand. In another embodiment, a suture is disposed about the stent in a crocheted manner, with the suture secured to an actuating member and a pull cord for releasing the crocheted structure being attached to another actuating member. When the pull cord actuating member is moved, the crocheted structure releases the stent, and the suture actuating member may be used to pull the suture free of the stent.

The above illustrative embodiments may comprise either over-the-wire structures in which the guidewire lumen extends from a proximal end of the catheter to a distal end of the catheter, or rapid-exchange or Monorail® configurations allowing a guidewire to exit the catheter shaft through a lateral opening distal of the proximal end. In some rapid-exchange embodiments, the guidewire exits adjacent the distal end of the catheter, with a very short distal portion distal of the stent disposed over the guidewire. In other rapid-exchange embodiments, the guidewire exits at a guidewire port disposed proximal of the stent.

Another illustrative embodiment includes a method of delivering a self-expanding stent by providing an elongate medical device including an inner multi-lumen member having at least a first lumen for receiving a guidewire and one or more ancillary lumens for receiving one or more actuating members. A hypotube is secured to the outside of the inner, multi-lumen member and extends for a majority of its length. The hypotube may be a micromachined member having a plurality of slots cut therein. The inner multi-lumen member may carry a constrained stent at or near its distal end. The method may further include placing the elongate medical device at a desired location and releasing the stent from its constrained position by manipulation of at least one actuating member.

BRIEF DESCRIPTION OF THE DRAWINGS

FIG. 1 is a perspective view of an illustrative embodiment;

FIG. 2 is a close view of a portion of the hypotube from FIG. 1;

FIG. 9 is a perspective view of another illustrative embodiment;

FIG. 10 is a longitudinal cross section of the distal end of the embodiment shown in FIG. 9;

FIG. 11 is an axial cross section of a portion of the embodiment shown in FIG. 9;

FIG. 12 is a perspective view of a portion of the inner tubular member from FIG. 9;

DETAILED DESCRIPTION

Figure 4:
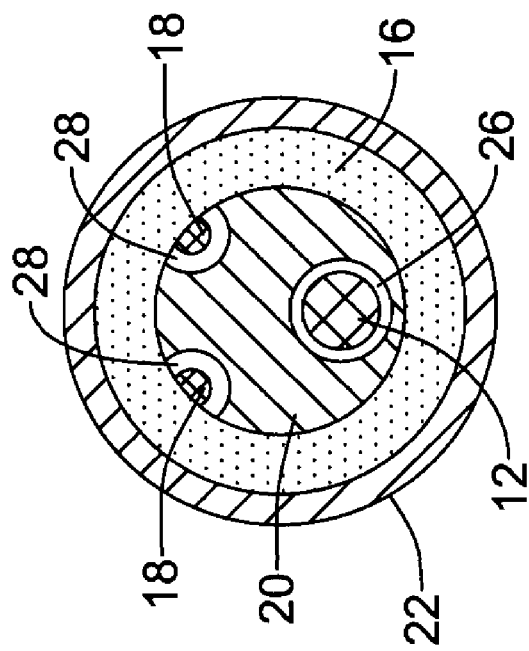
FIGS. 3-4 are axial cross-sectional views of the embodiment of FIG. 1.

The following detailed description should be read with reference to the drawings. The drawings, which are not necessarily to scale, depict illustrative embodiments and are not intended to limit the scope of the invention.

FIG. 1 is a perspective view of a distal end of an illustrative embodiment of a catheter 10. The catheter 10 may track a guidewire 12 and includes a self-expanding stent 14 disposed at a distal portion thereof. The self-expanding stent 14 is shown as being releasably retained in a constrained state by a sheath 16. The sheath 16 is coupled to actuating member(s) 18, which are used to control the location of the sheath 16 relative to the stent 14. The proximal end. (not shown) of catheter 10 may take any suitable form including, for example, such elements as a trigger, or a lever for actuating the actuating members 18. Although two actuating members 18 are shown, one or any other suitable number of actuating members may be provided. The device may be of a suitable size and length, for example, 45, 90 or 135 cm in length, and in the range of 1-14 French, although other sizes may be used.

The stent is releasably retained in its constrained state on an inner member 20. Proximal to the stent, the inner member 20 extends within and is secured to a hypotube 22. In some embodiments, the hypotube 22 extends for most of the length of the inner member 20. The inner member 20 may include or may be provided with a distal stop 24 to help keep the stent 14 in place. Manipulation of the actuating members 18 allows withdrawal of the sheath 16 in a proximal direction, releasing the stent. The stent may be any of a plurality of self-expanding forms that are well known in the art. Some illustrative examples include a Wallsten stent, as shown in U.S. Pat. No. 4,655,771, which is incorporated herein by reference, a woven member, or a structure made with a superelastic material. In some embodiments, the stent is a shape memory metal such as various Ni—Ti alloys, as are known in the art. The stent may also take the form of a stent-graft.

As illustrated in FIG. 2, the hypotube 22 may be a micromachined member having a plurality of partial cuts therein. This provides the hypotube with a form as shown in FIG. 2, where voids 42 define beams 44 that connect rings 46. This provides the hypotube 22 with increased bending flexibility while retaining substantial tensile strength. The hypotube 22 may be formed as set forth, for example, in U.S. Pat. No. 6,766,720; U.S. Pat. No. 6,579,246; and/or U.S. Pat. Application Pub. No. 2004/0181174A2, each of which is incorporated herein by reference. The hypotube 22 may be micromachined along a portion, several discrete portions, or substantially all of its length. In an illustrative example, at least a distal portion of the hypotube 22 is micromachined to facilitate the insertion of the distal portion through a tortuous portion of a patient's vasculature. The hypotube 22 may be formed of any suitable material, for example, a Ni—Ti alloy, a biocompatible stainless steel alloy, or a suitable polymer. The hypotube 22 may be coated, color coded, or otherwise modified as desired.

Figure 3:
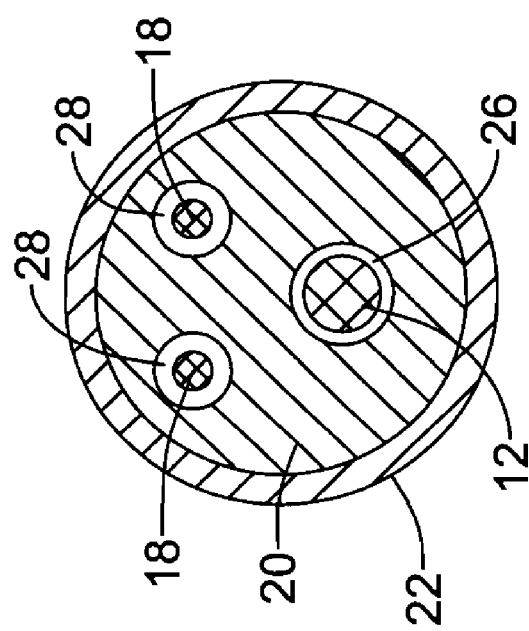

FIGS. 3-4 are axial cross-sectional views of the embodiment of FIG. 1. Referring to FIG. 3, the inner member 20 is shown having at least a guidewire lumen 26, which receives guidewire 12, and ancillary lumens 28, which receive the actuating members 18. The configuration, sizing and shape of the lumens 26, 28 may vary. Any of these lumens may be coated or provided with a liner to aid in slidable movement of the guidewire 12 or actuating members 18. Additional lumens may be provided, or one or more of the shown lumens 26, 28, may be used, for infusing fluids or for placement of other devices. This may include, for example, the placement of a coil for treating an aneurysm, infusion of contrast media to aid in visualization, or infusion of saline, heparinized saline, or other fluid for diagnostic or therapeutic purposes.

If desired, the inner member 20 may be secured to the hypotube 22 in several configurations and by several methods, for example, along a major portion of their coextensive length, at a single, relatively short distal section, or at several locations. This may be achieved, for example, by the use of an adhesive, which may be injected through the voids 44 (FIG. 2) in a micromachined hypotube 22. In some embodiments, a sleeve may be placed on the hypotube 22 and an appropriate adhesive may be injected thereunder such that capillary action draws the adhesive into contact with both the hypotube 22 and the inner member 20. In another embodiment, at least a distal portion of the hypotube is configured to be solid, such that capillary action can be used to draw adhesive under the solid portion of the hypotube to secure its distal end to the inner member 20.

Figure 18:
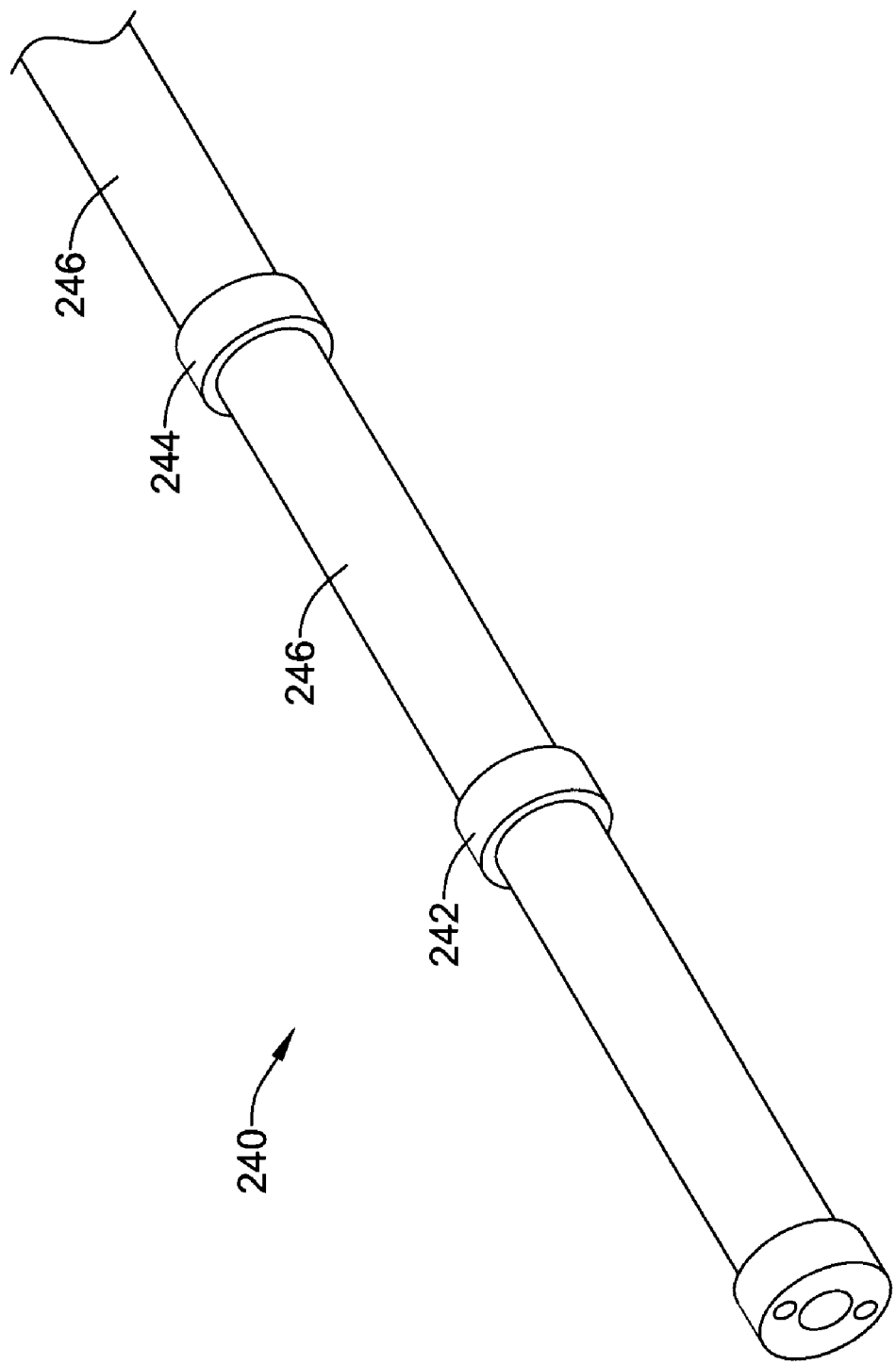
FIG. 18 is a perspective view of another configuration for an inner member.

In an illustrative example, the relative sizes of the hypotube 22 and the inner member 20 are selected such that, prior to bonding, the hypotube 22 is in sliding contact with substantially all of the outer circumference of the inner member, though this is not required. In another illustrative example, the inner member 20 may include ground portions having a reduced diameter to preserve greater bending flexibility at desired locations. Not only does such grinding increase the flexibility of the inner member 20, it also provides clearance that allows curvature of the hypotube 22 without interference from the inner member 20, which may become pinched as the hypotube 22 bends. In yet another illustrative example, the inner member 20 has a smaller outer diameter than the inner diameter of the hypotube 22, and one or more tubular members may be disposed between the hypotube 22 and the inner member 20 to bond the two together at selected locations. An illustrative example is shown in FIG. 18.

Some illustrative adhesives may be ultraviolet light curable adhesives, which may include polyurethanes, epoxies, acrylics and mixtures thereof. Other suitable adhesives may include heat curable, catalyst curable or moisture curable adhesives, such as cyanoacrylates, epoxies, hot melt adhesives, acrylics, silicones and mixtures thereof.

In another illustrative example, a heat process may be used to secure the inner member 20 directly to the hypotube 22. If heat is used or occurs during curing and/or as a securing step, one or more mandrels may be placed through the guidewire lumen 26 and/or ancillary lumens 28 during such heating to preserve lumen shape. For example, with mandrels disposed in the guidewire lumen 26 and/or ancillary lumens 28, and with longitudinal compression applied to the inner member 20 or a portion thereof, heat may be applied, causing the inner member 20 to expand into contact with the hypotube 22 at one or more locations or along a substantial length thereof, securing the inner member 20 to the hypotube 22.

As shown in FIG. 4, nearer the distal end of the hypotube 22, the catheter 10 includes sheath 16 extending between a narrowed portion of the inner member 20 and the hypotube 22. Because the sheath 16 is retracted onto this narrowed portion of the inner member 20, providing the hypotube 22 thereover may prevent difficulties in the retraction that can occur if foreign matter (such as a blood clot) becomes adhered to the inner member 20. Operation of an embodiment of this form is further illustrated by reference to FIGS. 19A-19B. An alternative form, wherein the sheath 16 does not retract beneath the hypotube 22, is shown in FIGS. 20A-20B.

In some embodiments, the inner member 20 is a single extrusion comprising a suitable biocompatible material such as a fluoropolymer, a block polyamide/polyether, high or low density polyethylene, or any other suitable material including a wide variety of polymers. The inner member 20 may also comprise multiple extruded members secured together. The inner member 20 may also comprise a coextruded member made of multiple materials, for example, using more lubricious material to form the interior of the guidewire lumen 26. The inner member 20 may include a stiffening member disposed therein, either as a part (i.e., a wire or tubular braid) onto which the inner member 20 is extruded, or as a discrete piece disposed in a lumen of the inner member 20.

Figure 5:
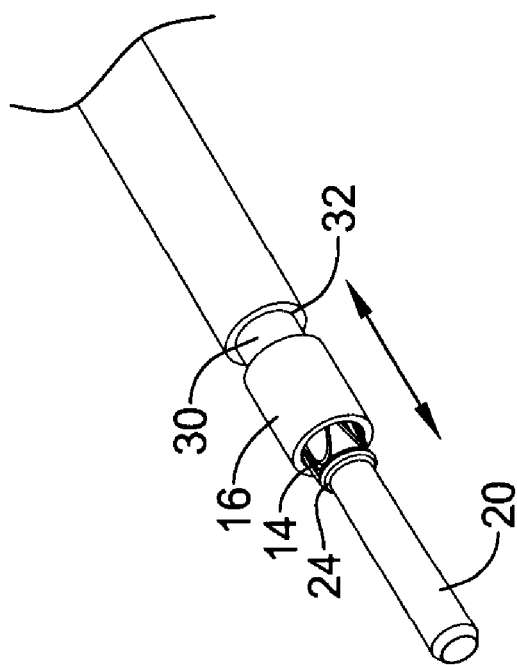
FIG. 5 is a perspective view as in FIG. 1 with the hypotube removed.

FIG. 5 is a perspective view as in FIG. 1 with the hypotube 22 removed. It can be observed from FIG. 5 that the sheath 16 may move over a proximal narrowed portion 30 of the inner member 20 from a distal position in which the stent 14 is fully constrained and ring 24 is covered, to a more proximal position in which the stent 14 is no longer constrained. A proximal annular ridge 32 may define the proximal limit of motion for the sheath 16.

Figure 6:
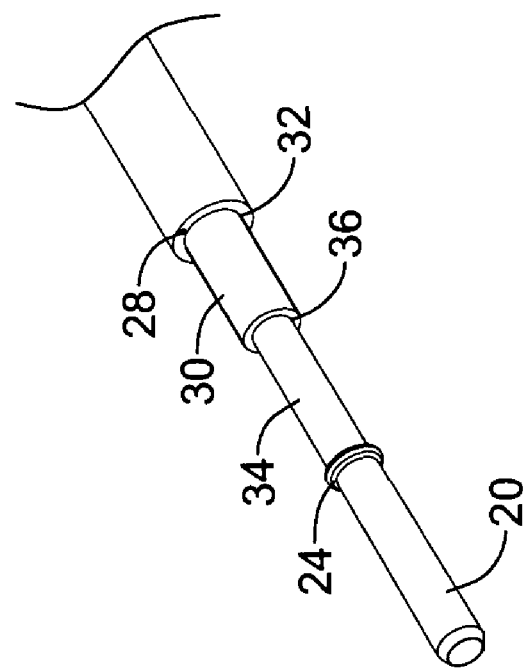
FIG. 6 is a perspective view of a portion of an inner tubular member from FIG. 1.

FIG. 6 is a perspective view of a portion of an inner member 20 from FIG. 1. It can be seen that the inner member 20 includes a distal narrowed portion 34 and a proximal narrowed portion 30. In some embodiments, one or more ancillary lumens 28 may open into the proximal annular ridge 32, or, alternatively, the ancillary lumen 28 may be accessible along the surface of the proximal narrowed portion 30. This latter form is generally shown in FIG. 4, while the former is in FIG. 6. A distal annular ridge 36, along with ring 24, defines a stent receiving section of the catheter on the distal narrowed portion 34. If desired, the ring 24 may comprise a radiopaque material to allow ready visualization of the distal end of the stent during delivery. If desired, the distal tip of the inner member 20 may simply be an extension of the inner member 20 itself, or it may be provided as a discrete piece of a softer material using any of a number of distal tips and distal tip attachment methods as are known for use in stent delivery catheters of a plurality of types. Radiopaque material may be added, or a ring provided, at the distal end as well.

Figure 7B:
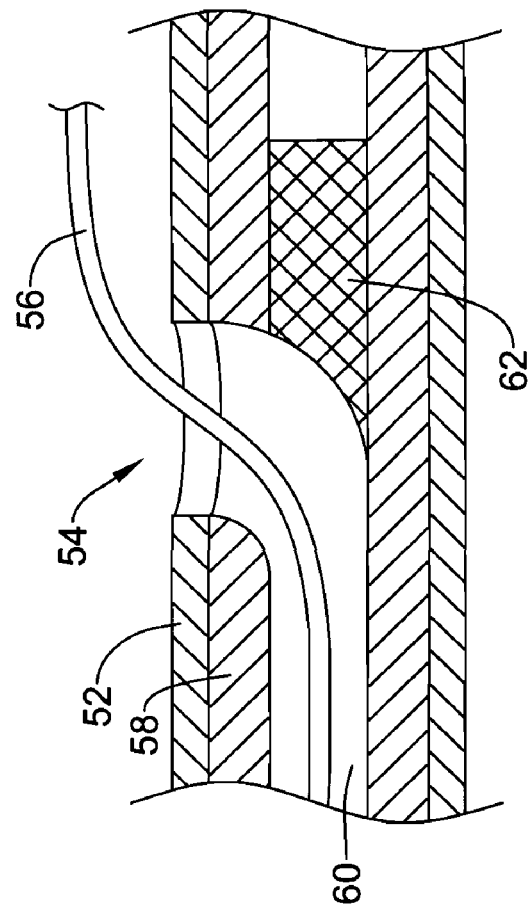
FIGS. 7A-7B are perspective and longitudinal cross-sectional views of a first rapid-exchange port.
Figure 7A:
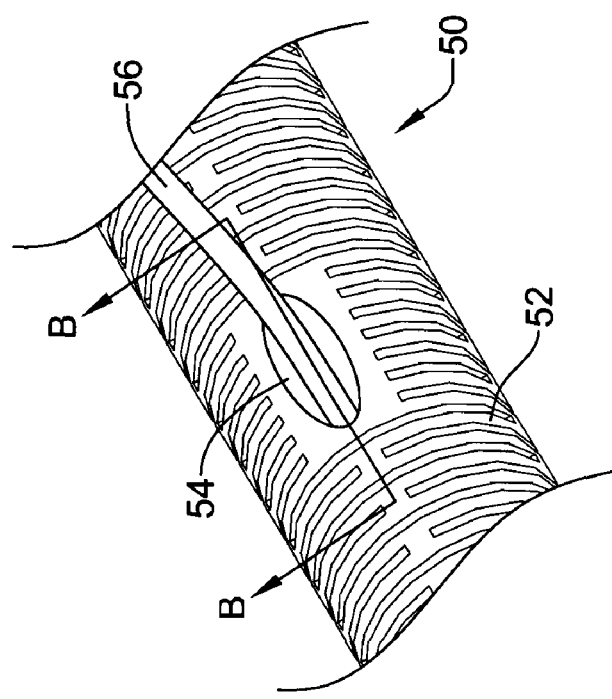

FIGS. 7A-7B are perspective and longitudinal cross-sectional views of a first rapid exchange port. In some embodiments, a rapid-exchange port is provided to allow easy exchange of catheters without requiring removal and replacement of the guidewire and/or the use of a guidewire extension. The embodiment shown in FIGS. 7A-7B illustrates one such rapid-exchange port, though other port designs may also be used.

The catheter 50 shown in FIGS. 7A-7B includes a hypotube 52 having a port 54 therethrough. Guidewire 56 is shown entering the catheter 50 at port 54 and extending distally therefrom, preferably to a location at or near the distal end (not shown) of the catheter 50. An opening is formed through the hypotube 52 as well as through the inner member 58 into the guidewire lumen 60. If desired, a ramp or plug member 62 may be inserted into the guidewire lumen 60 to force the guidewire 56 out of the lumen 60 and catheter 50. This is one manner of allowing back-loading of the guidewire 56 by inserting the proximal end of the guidewire 56 into the distal end of the catheter 50.

Figure 8B:
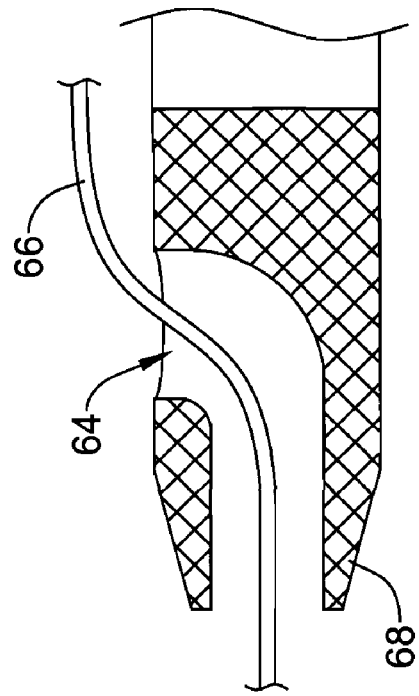
FIGS. 8A-8B are perspective and longitudinal cross-sectional views of a second rapid-exchange port.
Figure 8A:
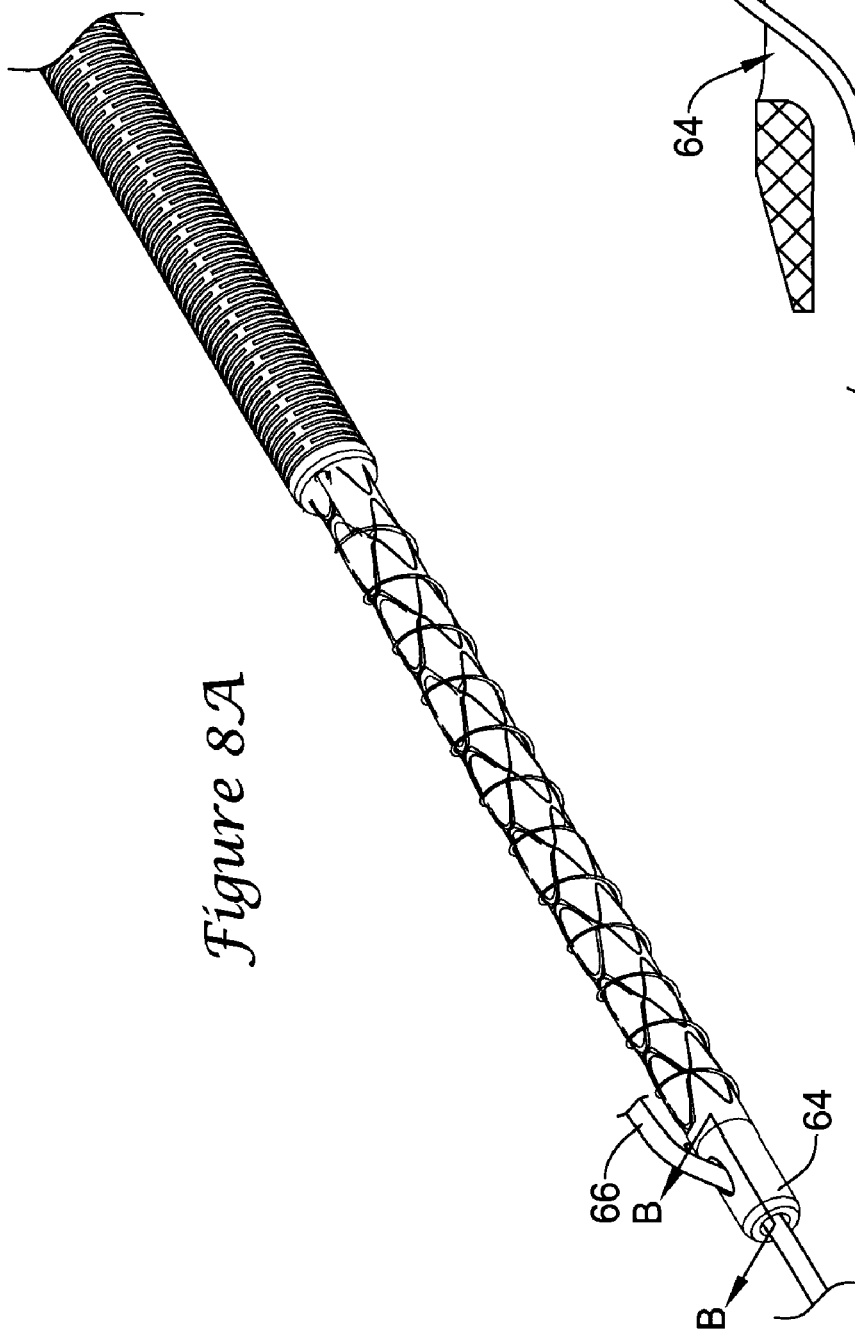

FIGS. 8A-8B are perspective and longitudinal cross-sectional views of a second rapid-exchange port. In this embodiment, the rapid-exchange port 64 is formed distal of the stent, within the last few centimeters of the distal end of the catheter. Thus, the guidewire 66 is only in a very distalmost portion of the catheter. In the embodiment shown in FIGS. 8A-8B, a separate piece 68 is provided at the distal tip to allow this form. Such an embodiment allows the guidewire lumen to be omitted from the proximal portion of the catheter, which may allow a reduced proximal diameter. In another embodiment, a plug is inserted into the guidewire lumen in a manner analogous to that of FIGS. 7A-7B.

FIG. 9 is a perspective view of another illustrative embodiment. In this embodiment, the catheter 70 includes a guidewire lumen that receives guidewire 72. A helically wound structure 74 restrains the stent 76 on the inner member 78 near its distal end. An elongate actuating member 80 is secured to the helically wound structure 74. Withdrawal of the actuating member 80 in a proximal direction unwinds the helically wound structure 74, allowing the stent to expand. A hypotube 82 extends over the inner member 78 and adds to its tensile strength. Again, the hypotube 82 may be a micromachined member. The wound structure 74 may be formed of a thin wire or a suture. In one embodiment, the wound structure 74 is a dissolvable suture that remains in the body, becoming stuck between the stent 76 and a surrounding vessel once the stent 76 is deployed. In another embodiment, the wound structure is a thin, very slippery strand (for example, of an appropriate, highly lubricous polymer) that is removably secured to the distal end of the inner member 78 and is removed by continued withdrawal of the actuating member 80 in a proximal direction.

FIG. 10 is a longitudinal cross section of the distal end of the embodiment shown in FIG. 9. As can be seen, the distal end of the helically wound structure 74 is secured into the distal end 84 of the inner member 78 to constrain the stent 76. In an illustrative embodiment, the helically wound structure 74 is a suture or thread or strand that is removably secured to the distal end 84. In another embodiment, the proximal end of the helically wound structure 74 is removably secured to an actuating member 80 (FIG. 9), such that it may be withdrawn from the distal end. In some embodiments, the stent 76 is allowed to expand beginning from its proximal end, rather than the distal end as may occur with a sheath as shown in FIG. 1. Because the hypotube 82 provides longitudinal support to its distal end, which is near or even adjacent the proximal end of the stent 76, this may achieve a relatively more accurate stent 76 placement as the location of initial contact between the stent 76 and the blood vessel is closely controlled.

FIG. 11 is an axial cross section of a portion of the embodiment shown in FIG. 9. The catheter includes inner member 78 that defines an ancillary lumen 86, containing the actuating member 80, as well as a guidewire lumen 88, which contains guidewire 72. The shape, size and location of lumens 86, 88 may vary. The hypotube 82 is shown generally closely disposed on the inner member 78, though this need not be the case along the entire length thereof.

FIG. 12 is a perspective view of a portion of the inner member from FIG. 9. The inner member 78 includes an annular ridge 90, with a narrowed portion 92 extending distally therefrom. The narrowed portion 92 is adapted to receive the stent (not shown) between the annular ridge 90 and distal tip portion 84, which may include a proximally facing annular ridge 94. The distal tip portion 84 may be a discrete piece secured to the inner member 78, or it may be a formed part of the inner member 78. The narrowed portion 92 may be formed by an appropriate removal process such as grinding, or by any other suitable method. Alternatively, the narrowed portion 92 may itself be a discrete part of the inner member 78, with the tip 84 and narrowed portion 92 either being a single piece or multiple discrete parts of the inner member 78.

Figure 13:
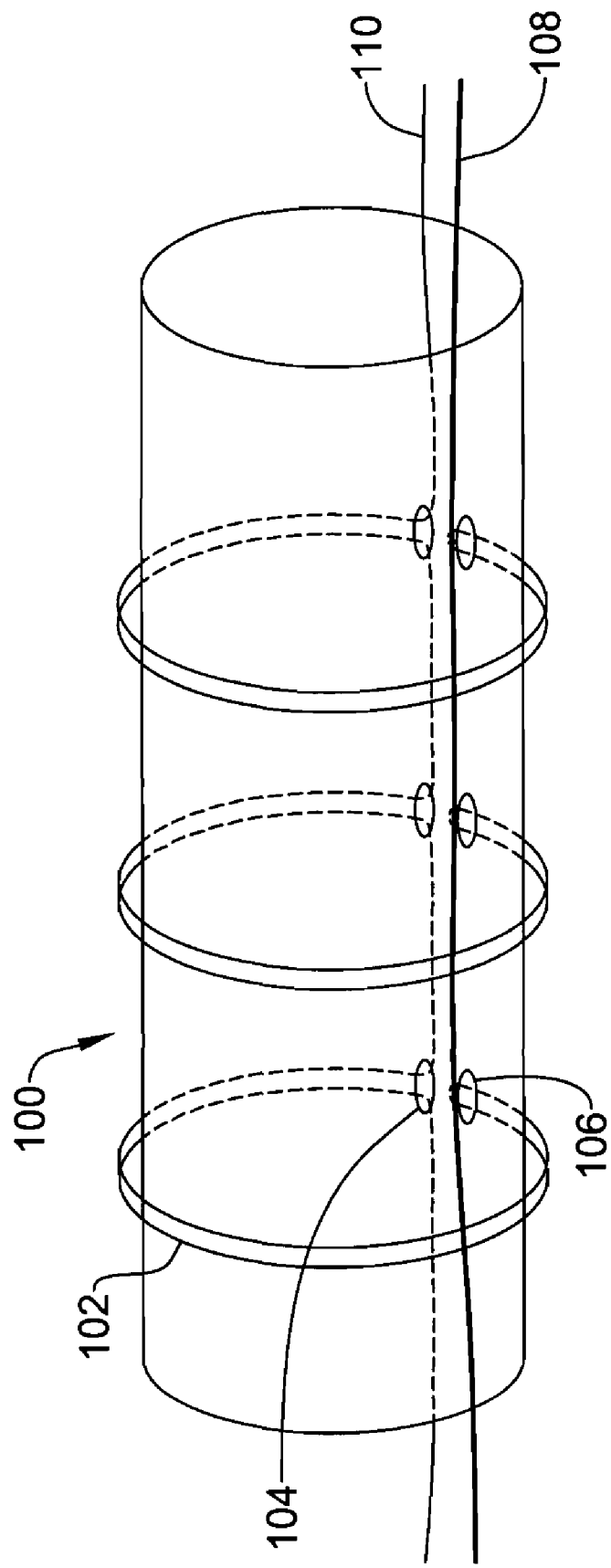
FIG. 13 is a perspective view of an illustrative stent constrained by a crocheted member.

FIG. 13 is a perspective view of an illustrative stent constrained by a crocheted member. The stent 100 is shown as a generic tubular member. A thread or strand 110 is shown as forming loops 102, with the strand 110 longitudinally extending within the stent 100, exiting to the exterior of the stent 100 at location 104, and forming a loop that extends into the stent 100 again at location 106. The loop 102 intersects pull cord 108, exits, and then wraps back around the stent 100 to reenter at location 104.

For example, the stent 100 may be a self-expanding stent in the form of a stent-graft, a drug-coated stent, or a bare stent. The crocheted structure may be added when the stent is in a non-expanded state, for example, while constrained or crimped under external pressure, or, if a shape memory metal is used, while in a reduced diameter state. After the crocheted structure is complete, the stent is allowed to exert pressure on the strand 110. When the strand 110 and pull cord 108 are disposed as shown, with the proximal and distal ends of the strand 110 secured, the stent 100 is releasably restrained in a compressed configuration.

To release the stent 100, the pull cord 108 is removed by pulling it in a longitudinal direction, releasing the loops 102 and allowing the stent 100 to expand. If the strand 110 is under tension when the pull cord 108 is removed, the stent may expand without trapping the strand 110, though this is not necessarily the case. This is one form of a "crocheted" structure that releasably restrains a stent. Additional crocheted structures are shown in U.S. Pat. No. 6,485,515, the disclosure of which is incorporated herein by reference.

Figure 14:
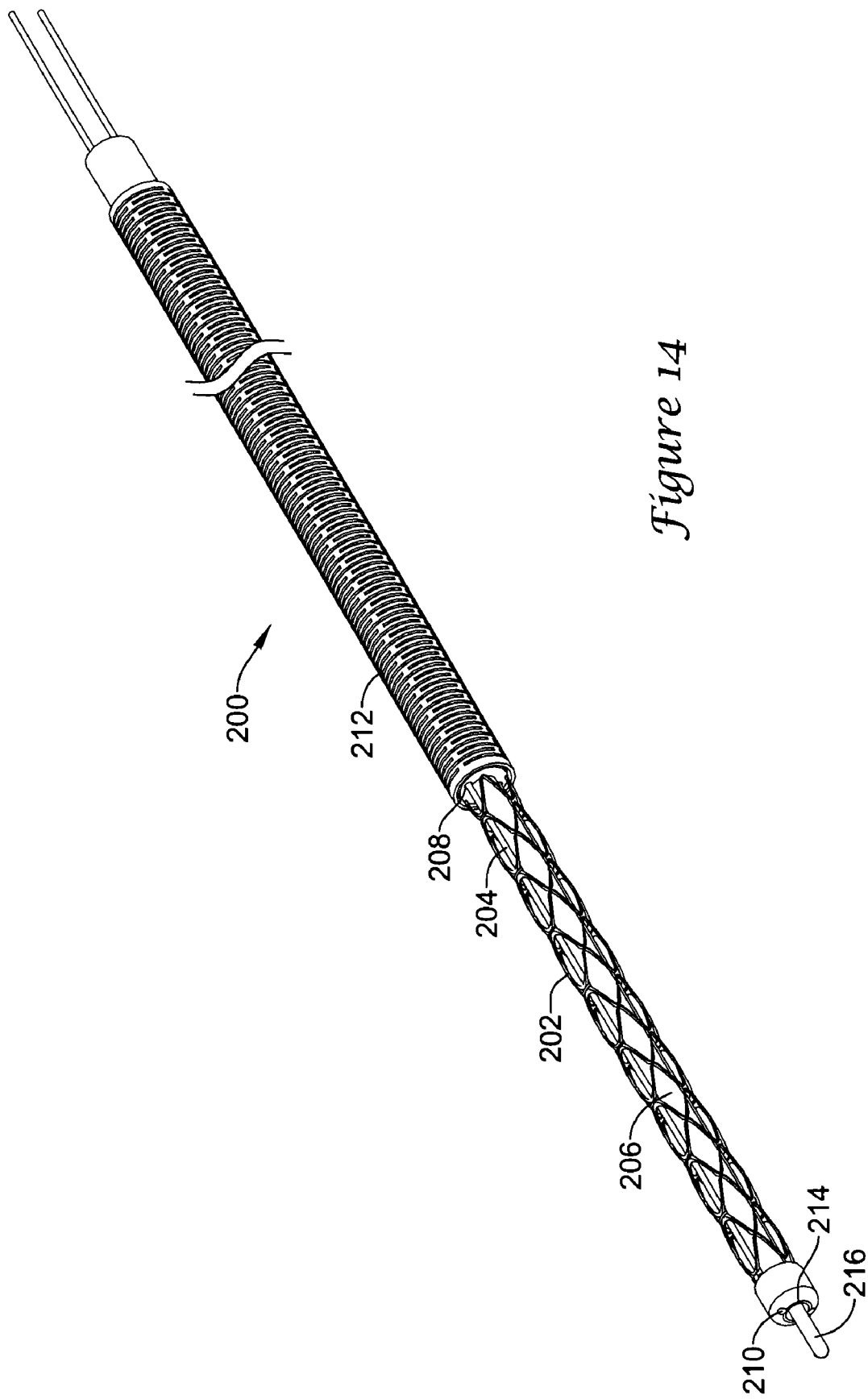
FIG. 14 is a perspective view of another illustrative embodiment.
Figure 16:
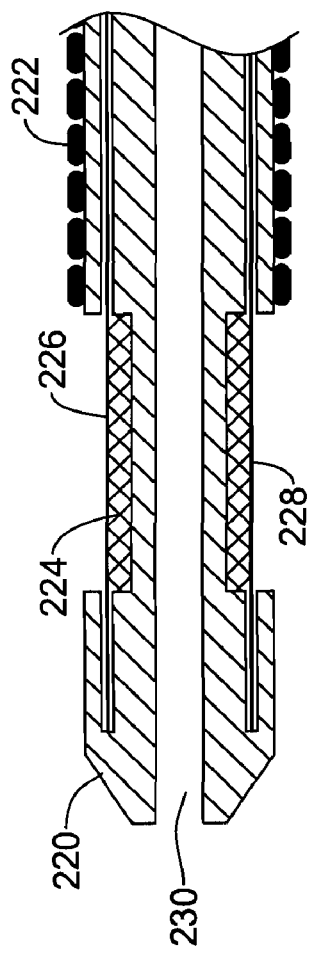
FIGS. 16-17 are longitudinal cross-sectional views illustrating a method of releasing a stent constrained by retaining wires.
Figure 17:
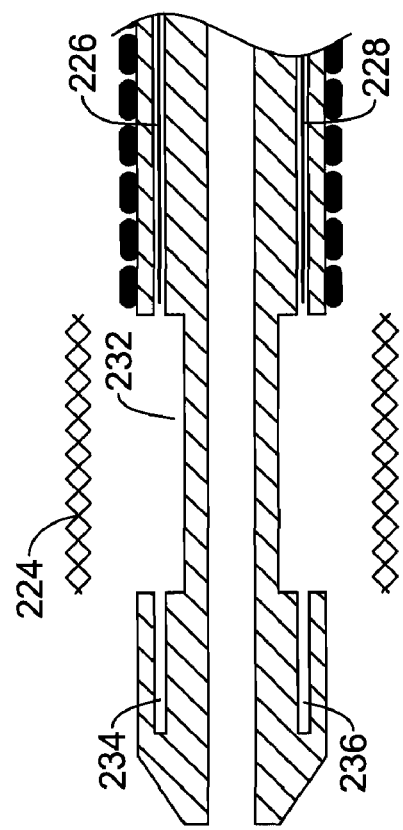

FIG. 14 is a perspective view of another illustrative embodiment. In this embodiment, the catheter 200 carries a stent 202 that is constrained by retaining wires 204 over an inner member 206. The retaining wires 204 exit the inner member 206 at location 208 and reenter to holes 210 at the distal end of the catheter. The holes 210 are receiving locations for the retaining wires 204, allowing the retaining wires 204 to hold the stent in place by providing distal support to the wires 204. As before, the inner member 206 is secured to a hypotube 212, which may be a micromachined member, and includes a guidewire lumen 214 that houses guidewire 216. FIGS. 16-17 illustrate a method of releasing the stent 202.

Figure 15:
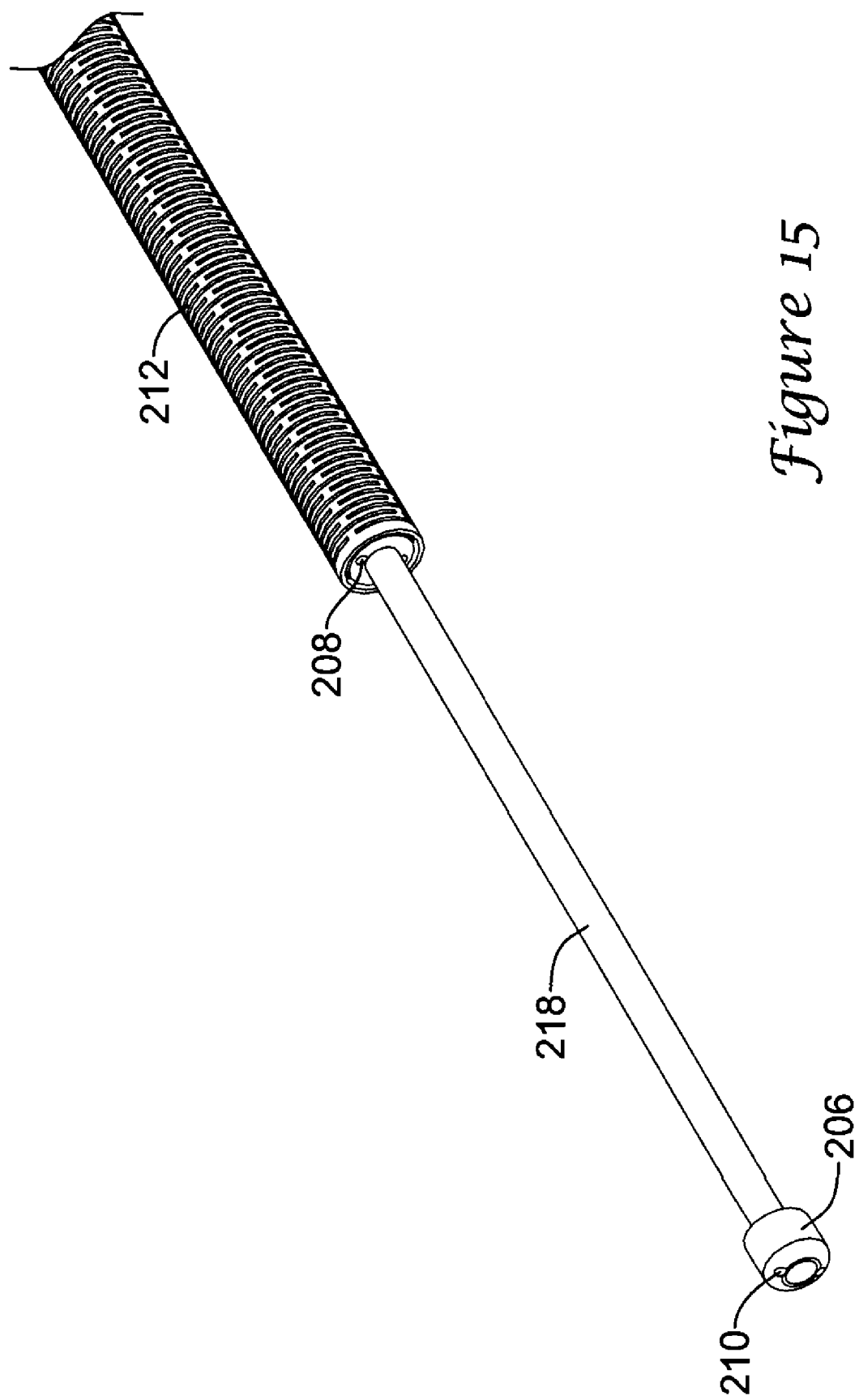
FIG. 15 is a perspective view of a portion of the device of FIG. 14.

FIG. 15 is a perspective view of the inner member 206 and hypotube 212 from FIG. 14. As can be seen, the inner member 206 includes a distal ground portion 218 that receives the stent (FIG. 14). The inner member 206 may be an extruded piece such that, prior to grinding to remove a distal portion, openings 208 and 210 are simply different parts of the same ancillary lumen. In another embodiment, the inner member 206 is formed of two or more pieces that are secured together.

FIGS. 16 and 17 are longitudinal cross-sectional views illustrating a method of releasing a stent constrained by retaining wires. In the illustrative embodiment, an inner member 220 with a micromachined hypotube 222 disposed thereon has a stent 224 restrained by retaining wires 226, 228. The inner member 220 may also define a guidewire lumen 230. Although only two retaining wires 226, 228 are shown in FIG. 16, additional retaining wires may also be provided. The retaining wires 226, 228 exit the interior of the inner member 220, extend over the stent 224, and reenter the inner member 220.

Referring to FIG. 17, the stent 224 has been released by withdrawing the retaining wires 226, 228 in a proximal direction. As can be seen, receiving locations 234, 236 are at the distal end of the catheter distal of the stent receiving portion 232. The receiving locations 234, 236 provide a structure that interacts with the distal end of the retaining wires 226 228. For example, the retaining wires 226, 228, may be relatively stiff wires coupled at their proximal ends to more flexible actuating members, which in turn extend toward or to the proximal end of the catheter shaft, so as to avoid compromising the flexibility of a proximal portion of the catheter shaft. Alternatively, the retaining wires 226, 228 may simply be an extension of the actuating members.

FIG. 18 illustrates another inner member 240 that may be used in place of any of inner members 20, 78 or 206. In this embodiment, the inner member 240 is provided with securing locations 242, 244 that are of a relatively larger diameter to allow for attachment of the hypotube (not shown). In between the receiving locations 242, 244, the inner member 240 includes a narrower diameter portion 246. In one embodiment, receiving locations 242, 244 are formed by placing a piece of polymeric material onto the inner member 240. The added piece may improve adhesion of the inner member 240 and the hypotube. In another embodiment, the inner member 240 is ground along a length 246. Either configuration allows for greater flexibility because the hypotube (not shown) will have available clearance to traverse a curvature relative to the inner member 240. The configuration of FIG. 18 is illustrative of forms that may be used for any of the other inner members shown in other illustrative embodiments.

Figure 19A:
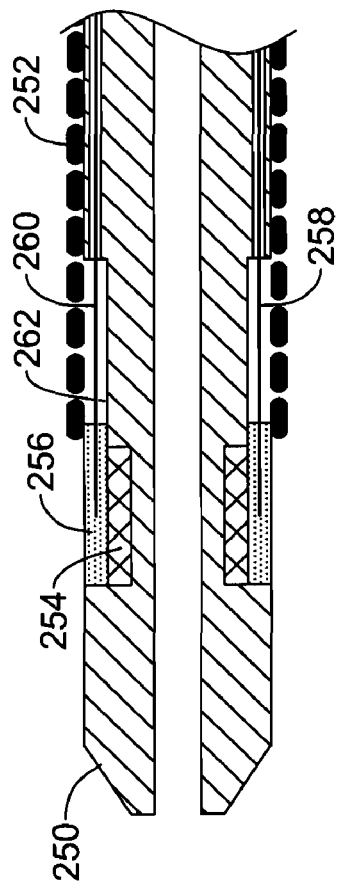
FIGS. 19A-19B are longitudinal cross-sectional views illustrating a device and method of releasing a stent constrained by a sheath.
Figure 19B:
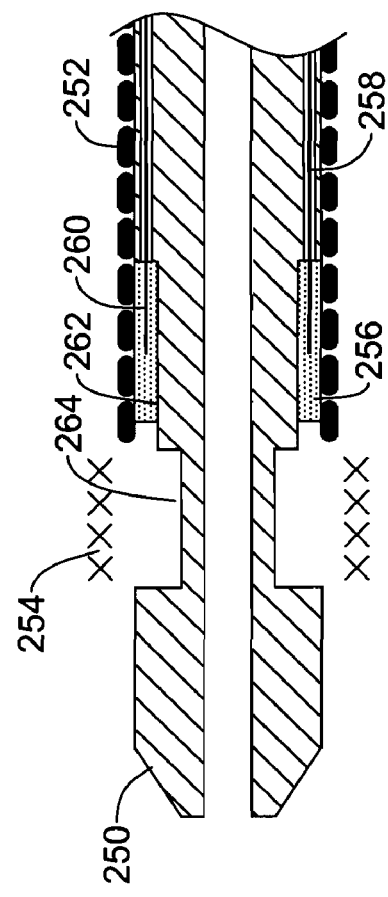
Figure 20A:
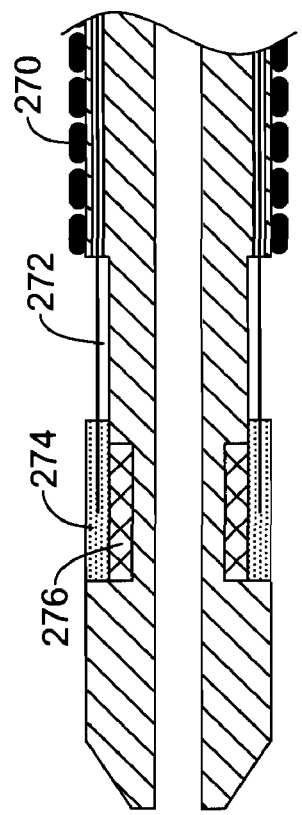
FIGS. 20A-20B are longitudinal cross-sectional views illustrating another device and method of releasing a stent constrained by a sheath.
Figure 20B:
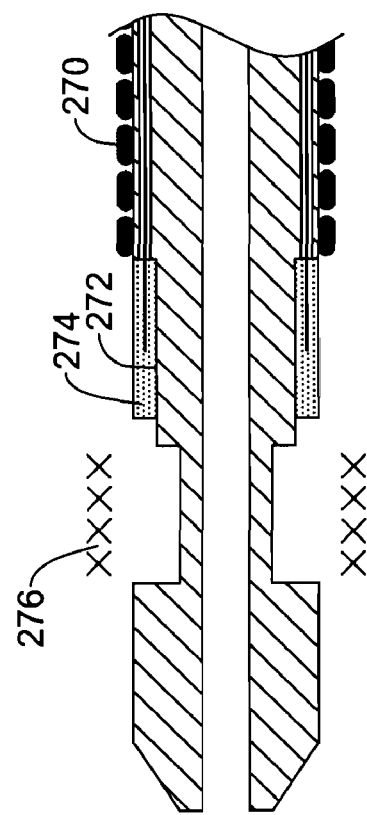

FIGS. 19A-19B are longitudinal cross-sectional views illustrating a method of releasing a stent constrained by a sheath. In this embodiment, the inner member 250 is secured to a hypotube 252. A stent 254 is restrained by sheath 256, which is secured to actuating members 258, 260. The sheath 256 is adapted to slide along surface 262, which extends beneath the hypotube 252. FIG. 19B illustrates release of the stent 254 from stent receiving portion 264 of the inner member 250. The sheath 256 is withdrawn to a space beneath the hypotube 252 along surface 262. By extending the hypotube 252 as shown, blood is prevented from coming into contact with surface 262, which may make retraction of the sheath 256 easier by preventing clots from accumulating in this region.

FIGS. 20A-20B are longitudinal cross-sectional views illustrating a method of releasing a stent constrained by a sheath. This embodiment is generally similar to that shown in FIGS. 19A-19B. However, in contrast to the illustrative example in FIGS. 19A-19B, the hypotube 270 does not extend over the region 272 that the sheath 274 retracts onto when releasing the stent 276. This design may be simpler to fabricate and, because a micromachined hypotube 270 is shown, may prevent the accumulation of material beneath the hypotube 270 if this is anticipated to be problem. For example, the hypotube may include voids (FIG. 2) that are sufficiently large to allow accumulation of blood between it and the structure below, such that an open structure as shown in FIGS. 20A-20B is advisable. This may depend on the particular micromachined hypotube 270.

Figure 21:
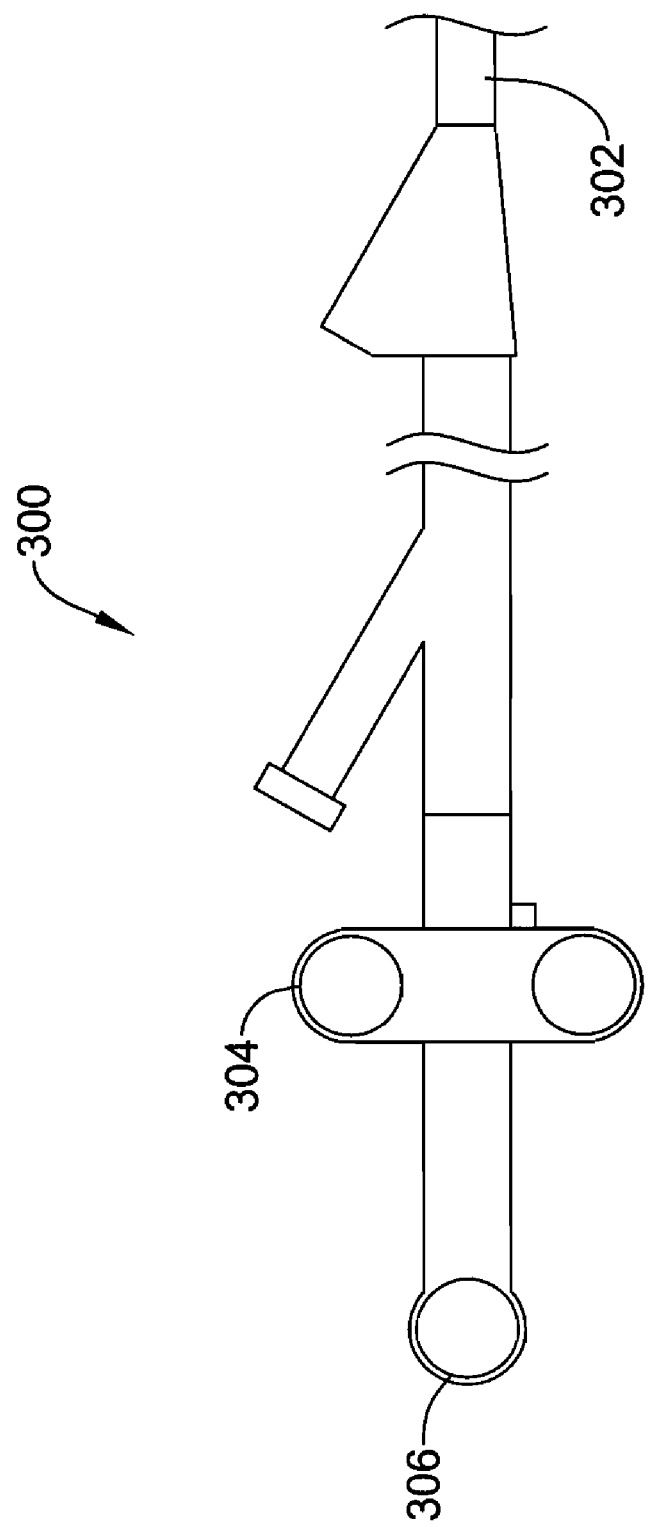
FIG. 21 is an illustrative proximal end for a catheter as in any of the above illustrative examples.

FIG. 21 is an illustrative proximal end for a self-expanding stent delivery catheter. The illustrative proximal end includes a manifold 300 secured to the catheter shaft 302. The manifold 300 includes a thumb receiver 306 and finger receivers 304. The finger receivers 304 are secured (internally to the manifold) to the actuating members (not shown). As the finger receivers 304 are retracted relative to the thumb receiver 306, the actuating members cause a stent located near the distal end of the catheter to be released. The manifold 300 may be located proximally of a Y-adaptor (not shown) separately allowing access to the guidewire lumen, or the manifold may be adapted to receive and pass the guidewire separately therethrough. Other manifold configurations may be used, and that shown is merely illustrative of one solution.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A catheter adapted for delivering a stent or stent-graft, the catheter comprising:
   an inner member defining at least a guidewire lumen and one or more ancillary lumens, the inner member including proximal and distal ends;
   one or more actuating members extending in the ancillary lumens;
   a micro-machined hypotube having a plurality of openings defined therethrough disposed on the outside of the inner member and secured thereto;
   a stent releasably secured near the distal end of the inner member; and
   a retaining member having at least a first state and a second state,
   wherein in the first state at least a portion of the retaining member is in direct contact with the stent,
   in the second state at least a portion of the retaining member is underneath the hypotube,
   the retaining member coupled to at least one of the one or more actuating members allowing a user, from a proximal end, to actuate the retaining member between the first state and the second state and release the stent.

2. The catheter of claim 1, wherein the hypotube is secured to the inner member at a plurality of locations along the length thereof.

3. The catheter of claim 1, wherein at least part of the inner member extends within the hypotube and includes a first region having a relatively smaller diameter and a second region having a relatively greater diameter, the hypotube being secured to the second region.

4. The catheter of claim 1, wherein the hypotube is secured to the inner member near the distal end thereof.

5. The catheter of claim 1, wherein:
   the inner member includes a receiving portion for receiving a stent thereon; and
   the catheter includes one or more receiving locations for receiving distal ends of at least one of the one or more actuating members, such that when a stent is disposed in the receiving portion, at least one actuating member extends thereover to a receiving location where the actuating member is removably received.

6. The catheter of claim 1, the retaining member comprising a sheath adapted to be moveably disposed over the stent to releasably retain it at a location relative the inner member, wherein at least one of the one or more actuating members is secured to the sheath.

7. The catheter of claim 6, wherein the inner member includes a proximal reduced outer diameter portion adjacent a distal reduced outer diameter portion such that the proximal reduced outer diameter portion extends beneath the hypotube, the sheath being moveable between a position over the distal reduced outer diameter portion and the proximal reduced outer diameter portion to allow a stent releasably retained on the distal reduced outer diameter portion to be released therefrom.

8. The catheter of claim 6, wherein the sheath is disposed distally of the hypotube in both an extended position for restraining the stent and a retracted portion for releasing the stent.

9. A catheter adapted for delivering a stent or stent-graft, the catheter comprising:
   an inner member defining at least a guidewire lumen and one or more ancillary lumens, the inner member including proximal and distal ends;
   one or more actuating members extending in one or more ancillary lumens;
   a hypotube disposed on the outside of the inner member and secured thereto;
   a stent; and
   a sheath for releasably retaining a stent on the distal end of the inner member, having at least a first state and a second state,
   wherein in the first state at least a portion of the sheath is in direct contact with the stent, in the second state at least a portion of the sheath is underneath the hypotube, the sheath for releasably retaining a stent being coupled to at least one of the one or more actuating members allowing a user, from a proximal end, to actuate the sheath for releasably retaining a stent.

10. The catheter of claim 9, wherein the hypotube comprises a micromachined hypotube including a plurality of openings defined therethrough.

* * * * *